United States Patent [19]

Fukaya et al.

[11] Patent Number: 5,609,825
[45] Date of Patent: Mar. 11, 1997

[54] OXYGEN SENSOR

[75] Inventors: Tomoji Fukaya, Kariya; Naoto Miwa, Tsushima, both of Japan

[73] Assignee: Nippondenso Co., Ltd., Kariya, Japan

[21] Appl. No.: 468,761

[22] Filed: Jun. 6, 1995

[30] Foreign Application Priority Data

Jun. 7, 1994 [JP] Japan ..................................... 6-150373

[51] Int. Cl.$^6$ .................................................... G01N 27/26
[52] U.S. Cl. ............................. 422/90; 204/421; 204/424
[58] Field of Search ............................. 422/90; 219/205, 219/206, 207, 541, 542, 548; 338/302, 303, 305, 331; 204/421, 424, 425, 426, 427, 428, 429

[56] References Cited

U.S. PATENT DOCUMENTS

| 475,169 | 5/1892 | Watson et al. ........................... 219/541 |
|---|---|---|
| 4,155,827 | 5/1979 | Mauer et al. ............................ 204/428 |
| 4,169,778 | 10/1979 | Mann et al. ............................. 204/429 |
| 4,175,019 | 11/1979 | Murphy .................................... 204/428 |
| 4,219,399 | 8/1980 | Gruner et al. ........................... 204/428 |
| 4,346,287 | 8/1982 | Desloge .................................... 219/541 |
| 4,362,605 | 12/1982 | Bozon et al. ............................ 204/428 |
| 4,383,906 | 5/1983 | Sano et al. ............................... 204/424 |
| 4,560,463 | 12/1985 | Frey et al. ................................ 204/424 |
| 4,578,174 | 3/1986 | Kao et al. ................................. 204/429 |
| 4,754,124 | 6/1988 | Howell et al. ........................... 219/523 |
| 4,824,550 | 4/1989 | Ker et al. .................................. 204/427 |
| 4,948,491 | 8/1990 | Kato et al. ................................ 204/424 |

FOREIGN PATENT DOCUMENTS

| 57-142555 | 9/1982 | Japan . |
|---|---|---|
| 58-172543 | 10/1983 | Japan . |
| 63-50798 | 12/1988 | Japan . |

Primary Examiner—Jill Warden
Assistant Examiner—Alexander Markoff
Attorney, Agent, or Firm—Cushman, Darby & Cushman IP Group of Pillsbury Madison & Sutro LLP

[57] ABSTRACT

To provide an oxygen sensor having a heater unit without being broken by vibration impact of a vehicle, the oxygen sensor includes a cylindrical oxygen detecting element with a closed bottom and a heater unit installed in an inside of the oxygen detecting element. The heater unit includes insulators, the heat generating body helically wound a surface thereof and lead wires. In the insulators, concave portions reaching lead holes are disposed. Lead wires are put through the lead holes from an outer circumferential surface. In the concave portions, the heat generating body and the lead wires are connected. The outer circumference of a winding portion of the heat generating body is preferably formed at a position more inwardly than the outer circumferential surface of the adjacent insulator.

6 Claims, 3 Drawing Sheets

5,609,825

OXYGEN SENSOR

CROSS REFERENCE TO RELATED APPLICATION

This application is based on and claims priority of Japanese Patent Application No. 6-150373 filed Jun. 7, 1994, the content of which is incorporated herein by reference.

BACKGROUND OF THE INVENTION

1. Field of the Invention

The present invention relates to an oxygen sensor which detects an air fuel ratio or the like of an automotive engine.

2. Description of Related Art

When the air fuel ratio of an internal combustion engine for a vehicle is not proper, not only the energy (fuel) is lost but also an air pollution is caused. Therefore, the air fuel ratio is detected by using an oxygen sensor. The oxygen sensor includes an electric chemical cell by installing electrodes on both sides of a solid electrolyte which is an oxygen ion conducting body. Exhaust gas is introduced in one side of the electrode and the air is introduced in the other side. Thus, the air fuel ratio of the internal combustion engine is detected from a potential difference between the electrodes produced by a concentration difference. In the solid electrolyte mentioned above, in order to produce oxygen ion conduction, high temperature is required and the above-mentioned cell is heated by using a heater.

As shown in FIG. 4, oxygen sensor 90 has oxygen detecting element 91 which has tubular shape with a closed end forming an electric chemical cell, and housing 92 holding oxygen detecting element 91. Housing 92 has body portion 93 having flange 931 at an approximately middle portion. Body portion 93 has element covers 941 and 942 being inserted into an exhaust air passage at a lower portion thereof and protection covers 951 through 953 contacting the air at the upper portion thereof.

Oxygen detecting element 91 is held at body portion 93 through insulating material 932. In the inside of oxygen detecting element 91, heater unit 96 is installed. Heater unit 96 includes, heat generating body 962, made of NICHROME wire, helically wound on the outer circumferential surface of insulator 961 porous insulating layers (not shown in figure) covering the outside of heat generating body 962 (see Japanese Patent Application Laid-open No. 58-172543). NICHROME is a registered trademark of the Driver-Harris Wire Company and relates to alloys of nickel, chromium and iron containing less than 30% iron.

In the method for winding the heat generating body on the outer circumferential surface, an assembly work is easy and heating efficiency is good. The reason why heat generating body 962 is covered with the insulating layers is to obtain an electric insulation with the inside electrode of oxygen detecting element 91.

On the inside portion of insulator 961, a lead hole inserting a lead wire not shown in figure is made and heat generating body 962 is connected to the lead wire and the lead wire is connected to an electric supply line through the lead hole. That is, a lead wire drawing-out hole communicating with the lead hole of the inside from the outer circumferential surface of insulator 961 is made. The lead wire is drawn out and an end portion of the lead wire and an end portion of the heat generating body are welded.

However, the following problem exists in the related art oxygen sensor. Since the oxygen sensor using for a vehicle is exposed under severe vibration for a long time by actuating automobiles, a joint portion of the heat generating body and the lead wire can be broken undesirably. Although a heat generating body and a lead wire such as a NICHROME wire or the like a NICHROME wire and a lead wire are connected firmly by being welded, they can be often broken due to vibration.

SUMMARY OF THE INVENTION

It is an object of the present invention to provide an oxygen sensor for a vehicle which is hardly broken and which has a heater unit with good heating efficiency.

The oxygen sensor in the present invention includes an oxygen detecting element having a cylindrical shape with a closed end and made of solid electrolyte, a housing holding the oxygen detecting element at a tip end side and a heater unit installed at an inside of the oxygen detecting element, the heater unit having first and second insulators having tubular-shape, a heat generating body helically wound at an outer circumferential surface of the second insulator and a pair of lead wires connected with the heat generating body, wherein the insulators have a lead hole to put the lead wires through and further have a pair of concave portions reaching the lead hole from the outer circumferential surface, and the lead wires and the heat generating body are connected at joint portions inside of the concave portions.

The most significant part of the present invention is that a pair of concave portions reaching the lead holes are made at the insulator of the heater unit and the heat generating body and the lead wires are connected on the inside of the concave portion. Since a pair of lead wires are necessary, two lead wires can be inserted in one lead hole though a pair of the lead holes are usually made.

The outer circumference of a winding portion of the heat generating body is positioned more inwardly than the outer circumferential surface of the basic end portion side adjacent thereto. Since the heat generating body is wound around a winding portion, an outer diameter becomes larger with the thickness thereof. Although the heat generating body becomes easy to contact an inside wall surface of the oxygen detecting element, the winding portion is installed inside as mentioned above. Therefore, the heat generating body can be prevented from coming off. The outer circumference of the winding portion having more than the thickness of the heat generating body is arranged inside, thereby, the heat generating body can be prevented from projecting from the outer circumferential surface next thereto. Also, the heat generating body is preferably made of KANTHAL (iron, chrome, aluminum alloy).

The KANTHAL can form an aluminum oxidation film easily on the surface thereof. Thus, by using the KANTHAL, in the same case as the NICHROME wire, the insulating layers do not have to be installed separately on the surface so as to obtain the electric insulation to the inside electrode of the oxygen detecting element. In this case, a clearance between the KANTHAL heat generating body and the inside electrode of the oxygen detecting element is ranged from 0.1 to 0.3 mm preferably. The aluminum oxidation film formed on the surface of the KANTHAL should not contact the inside of the oxygen detecting element since the film is thin. Considering vibration of a vehicle and a heat expansion of the heat generating body, the clearance is preferably set to 0.1 mm or more. However, when the clearance is too large, the heating efficiency of the heater unit decreases. Therefore, the clearance is set to 0.3 mm or less preferably.

In the heater unit of the oxygen sensor in the present invention, concave portions are made at an insulator and joining the heat generating body and a lead wire is in the concave portions. That is, the joint portions of the heat generating body and each end of the lead wire are inside of outer circumferential surfaces of the concave portions, that is, the insulator, and therefore, the joint portions do not project from the outer circumferential surface of the insulator. Thus, the joint portions do not contact an inside wall surface of the oxygen detecting element and breaking at the joint portions is hard to occurred.

The inventors researched causes of the breaking of the joint portions of the heat generating body and the lead wire in the related art oxygen sensor and found out that contacting the inside wall surface of the oxygen detecting element produced by vibration of a vehicle was the main cause of the breaking.

Therefore, by forming the joint portions inside of the concave portions, contacting the inside wall surface of the oxygen detecting element is stopped and the joint portions can be prevented from breaking. Further, in the heater unit in the present invention, since the heat generating body is formed to be wound at the outer circumferential surface of the insulator, an assembly work of the heat generating body is simplified and a man-hour is reduced. Moreover, by using KANTHAL for the heat generating body, the insulating layers of the surface do not need as mentioned above and the inside of the oxygen detecting element is heated directly. Therefore, the heating efficiency can be good.

According to the present invention as mentioned above, even though the oxygen sensor is used for a vehicle having much vibration, it does not break in any part and a heater unit with good heating efficiency having an oxygen detecting sensor can be provided.

DETAILED DESCRIPTION OF THE PREFERRED EMBODIMENTS

The present invention will be described in detail with reference to the accompanying FIGS. 1 through 3.

Figure 1:
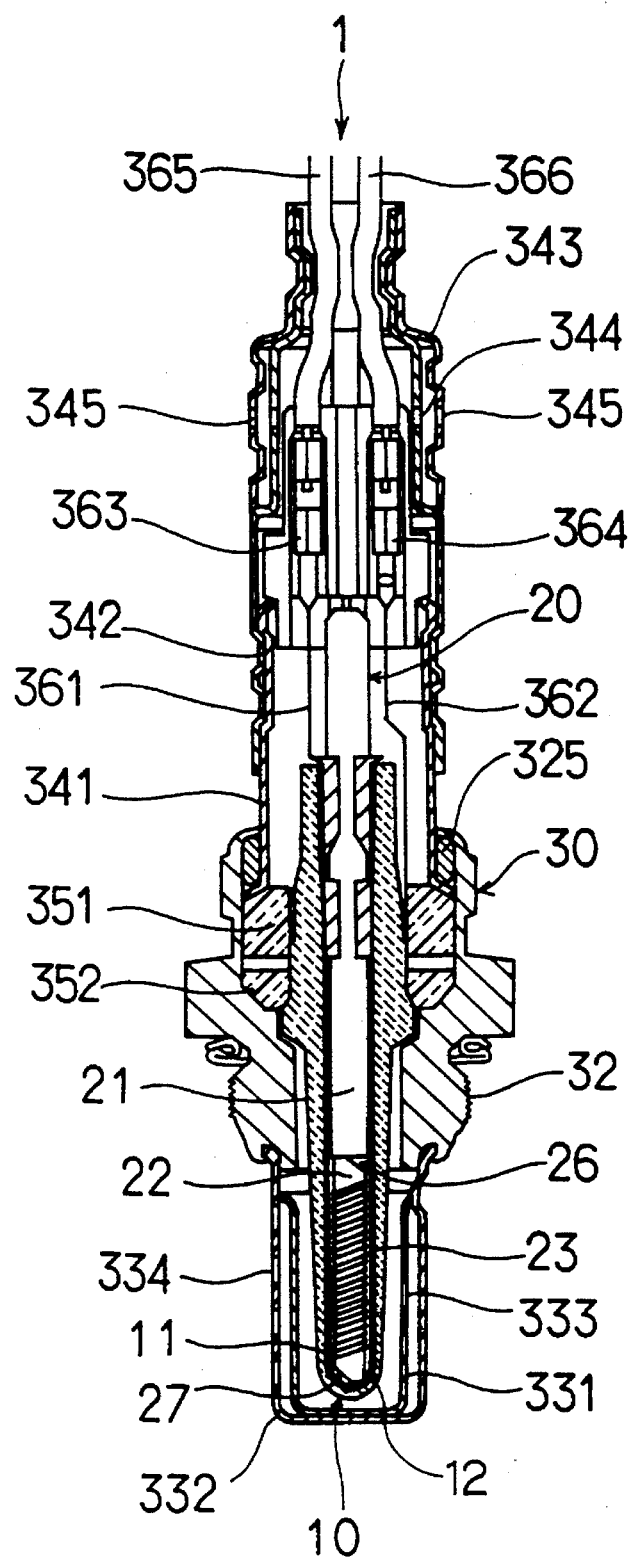
FIG. 1 is a longitudinal sectional view illustrating an oxygen detecting sensor in the embodiment of the present invention.

As shown in FIG. 1, oxygen sensor 1 has oxygen detecting element 10 having cylindrical solid electrolyte 11 with a closed bottom, housing 30 holding oxygen detecting element 10 at a tip end side and heater unit 20 arranging oxygen detecting element 10 on the inside.

Figure 2:
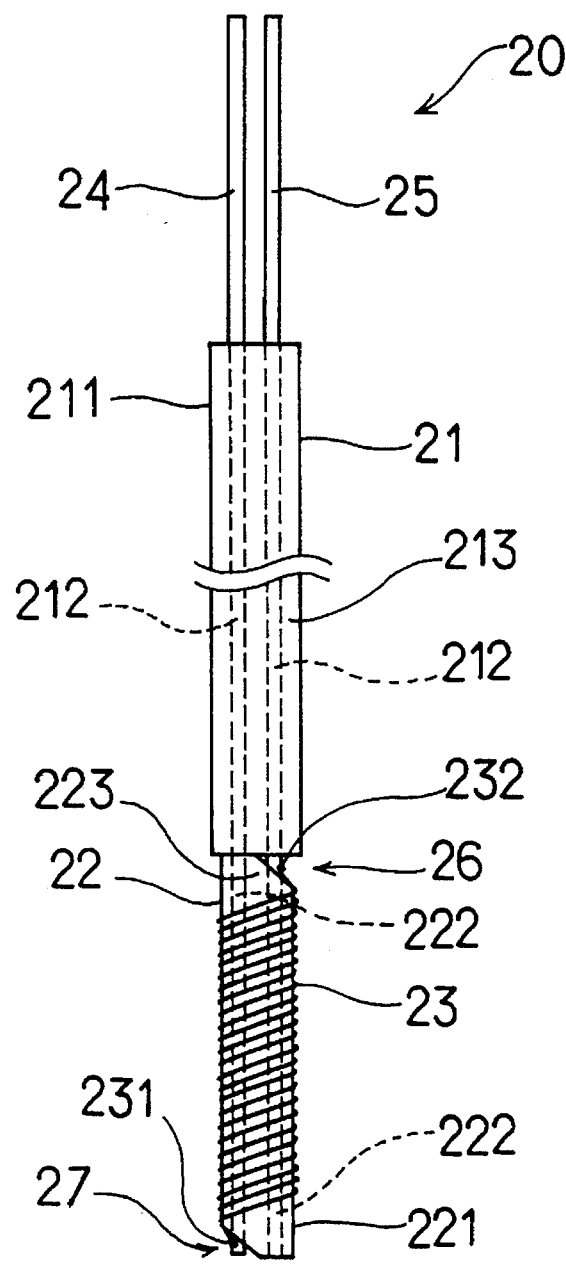
FIG. 2 is a front view illustrating a heater unit in the embodiment.
Figure 3:
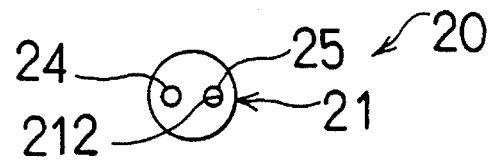
FIG. 3 is a plan view illustrating the heater unit in the embodiment.
Figure 4:
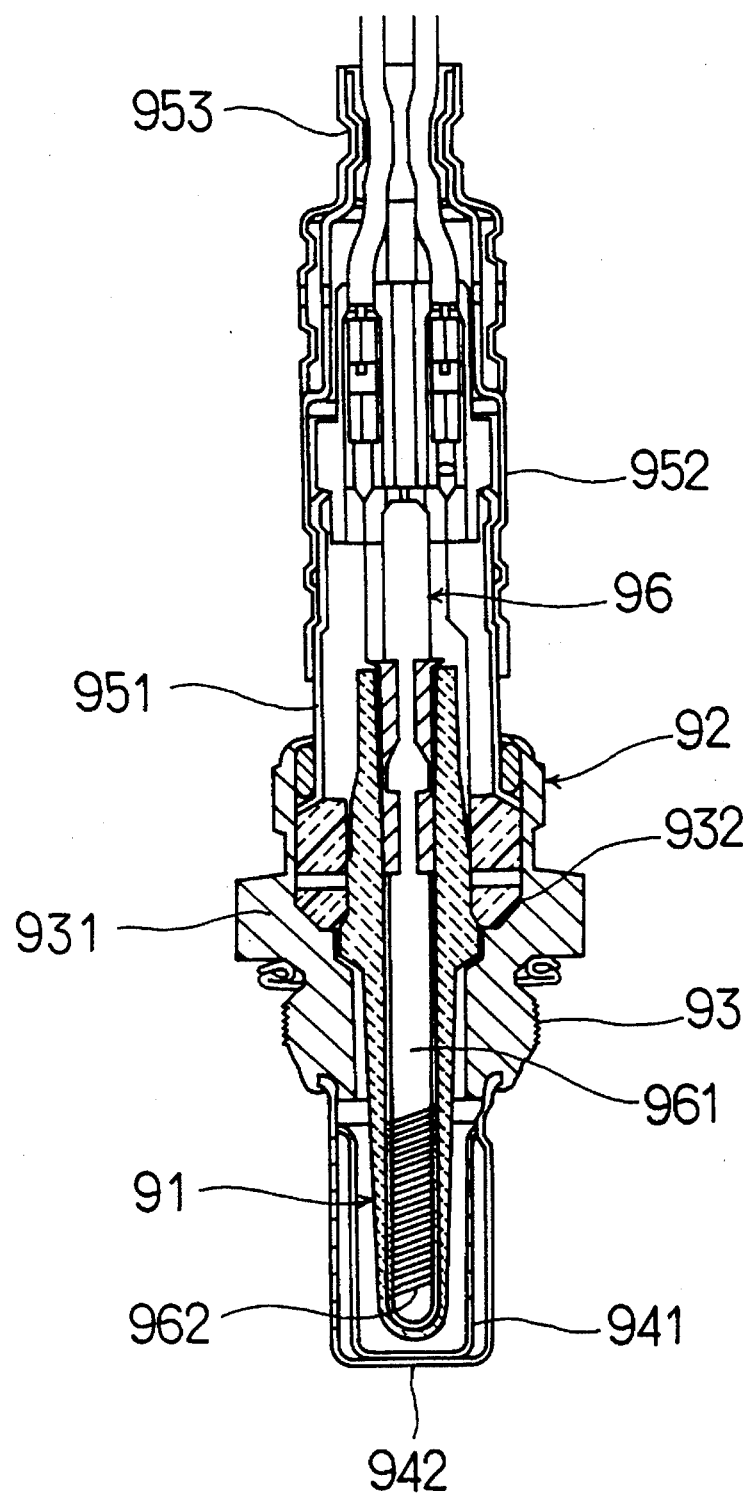
FIG. 4 is a longitudinal sectional view illustrating an oxygen sensor in the related art.

As shown in FIG. 2, heater unit 20 has first tubular insulator 21 and second tubular insulator 22 having a smaller diameter than first insulator 21, heat generating body 23 being helically wound on second outer circumferential surface 223 of second insulator 22 to cover a tip side and lead wires 24 and 25 connecting heat generating body 23 to a electric supply line. In first and second insulators 21 and 22, a pair of lead holes 212 and 222 are formed. Each lead hole penetrates first and second insulators 21 and 22 straight. Lead wires 24 and 25 are inserted from base end 211 to tip end 221. Moreover, a pair of concave portions 26 and 27 reaching lead holes 212 and 222 from the outer circumferential surface are formed on second insulator 22. Heat generating body 23 and lead wires 24 and 25 are connected at joint portions 231 and 232. Heat generating body 23 is wound around second insulator 22, while second outer circumferential surface 223 is located at a position more inwardly than outer circumferential surface 213 of first insulator 21 adjacent to base end 211. Second outer circumferential surface 223 is located inside of first outer circumferential surface 213. The radius of second outer circumferential surface 223 is smaller than that of first outer circumferential surface 213 by at least a diameter of wire forming heat generating body 23. Heat generating body 23 is the helical wire made of KANTHAL (iron, chrome and aluminum alloy). Oxygen detecting element 10 has inside electrode 12 inside surface thereof. A clearance between heat generating body 23 and inside electrode 12 of oxygen detecting element 10 is ranged from 0.1 to 0.3 mm.

The following is explained separately.

In the embodiment, oxygen sensor 1 is to detect an air combustion ratio of an automobile engine. As shown in FIG. 1, housing 30 includes body portion 32 spirally attaching oxygen sensor 1 to an engine exhaust air passage and inside and outside element covers 331 and 332 inserted into the exhaust air passage and protection covers 341 through 343. On both element covers 331 and 332, vent parts 333 and 334 introducing exhaust gas is formed. In second and third protection covers 342 and 343 located at base end 211, air intakes 344 and 345 introducing the air to oxygen detecting element 10 are installed. Oxygen detecting element 10 is held at body portion 32 through insulating materials 351 and 352. Oxygen detecting element 10 includes cylindrical solid electrolyte 11 with a closed end and an electrode (not shown in figure) installed in an inside and an outside of solid electrolyte 11. Both electrodes are connected to signal wires 365 and 366 by way of wires 361 and 362 and relay terminals 363 and 364.

As shown in FIG. 2, heater unit 20 includes first insulator 21 having a major diameter and second insulator 22 having a minor diameter. In addition, heat generating body 23 is wound around lower portion of second insulator 22 and lead wires 24 and 25 are inserted through lead holes 212 and 222 inside of first and second insulators 21 and 22. Lower portion of second insulator 22 has a tip end 221 and an end portion on which concave portions 26 and 27 (notches) are formed. Concave portions 26 and 27 communicate with lead holes 212 and 222 respectively. One side of lead wire 24 is connected by welding with an end portion of heat generating body 23 at concave portion 27. One side of lead wire 25 is connected by welding with the other end portion of heat generating body 23 at concave portion 26. Moreover, other ends of both lead wires 24 and 25 are connected to an electric supply line not shown in figure.

Heat generating body 23 is a wire material made of KANTHAL. An aluminum oxidation film is formed on a surface of heat generating body 23 by heating or performing a conduction process at the temperature from 1000° to 1100° C. The radius of first insulator 21 is set to have a larger value than the radius of second insulator 22 by at least the value of the diameter of heat generating body 23. Further, a clearance between heat generating body 23 wound around insulator 22 and the inside electrode of oxygen detecting element 10 is preferably ranged from 0.1 to 0.3 mm. In FIG. 1, metal ring 325 is used for fixing oxygen detecting element 10 to housing 30 by heat-crimping.

Next, operation effects of oxygen sensor 1 of this embodiment is explained.

Heat generating body 23 of heater unit 20 of the embodiment is connected to lead wires 24 and 25 in concave portions 26 and 27 formed at second insulator 22, and further, joint portions 231 and 232 of heat generating body 23 are inside of outer circumferential surface 223 of second insulator 22. Therefore, even though oxygen sensor 1 obtains vibration and impact, joint portions 231 and 232 do not contact the inside wall of oxygen detecting element 10. Consequently, lead wires 24 and 25, and heat generating body 23 are hard to break at joint portions 231 and 232. Heat generating portion 23 is made of KANTHAL, thereby, an insulated aluminum oxidation film can be easily formed. Hence, an insulating layer made of other material need not be installed separately on the surface of heat generating body 23, thereby, production cost of heater unit 20 can be reduced.

Since a clearance between the surface of wound heat generating body 23 and the inside electrode of oxygen detecting element 10 is 0.1 mm or more, even though vibration impact is added to oxygen sensor 1, the surface of heat generating body 23 does not contact the inside of oxygen detecting element 10. Therefore, the aluminum oxidation film formed on the surface of the KANTHAL does not peel off. Since heat generating body 23 directly heats the inside of oxygen detecting element 10 through a thin aluminum oxidation film on heat generating body 23, the heating efficiency is extremely good. Heat generating body 23 is wound around insulator 22 and forming insulating layers at the surface of heat generating body 23 is not necessary, thereby, an assembly work is facilitated.

According to the embodiment as mentioned above, even though the unit is used for a vehicle having much vibration, there is no breaking in any part thereof. Moreover, an oxygen sensor having a heater unit with good heating efficiency can be provided.

What is claimed is:

1. An oxygen sensor comprising:

an oxygen detecting element having a cylindrical shape with a closed end and made of solid electrolyte;

a housing holding said oxygen detecting element;

a first insulator disposed within said oxygen detecting element and having an inner space therein;

a second insulator having a diameter smaller than that of said first insulator, said second insulator having therein an inner space, said second insulator including an opening through which said inner space of said second insulator communicates with said inner space of said first insulator;

a pair of lead wires inserted through said inner spaces of said first insulator and said second insulator; and a heating wire wound around said second insulator, wherein, said heating wire extends through said opening and is connected to said pair of lead wires.

2. An oxygen sensor according to claim 1, wherein two openings are formed on said second insulator, one being said opening through which said inner space of said second insulator communicates with said inner space of said first insulator and being formed around a connection portion between said first insulator and an end of said second insulator, and the other being formed at another end of said second insulator.

3. An oxygen sensor according to claim 1, wherein said inner space of said first insulator includes two lead holes through which said pair of lead wires are inserted, respectively.

4. An oxygen sensor according to claim 1 wherein, an outer circumferential surface of said second insulator is located more inwardly than an outer circumference of said first insulator by at least a diameter of said heating wire.

5. An oxygen sensor according to claim 1, wherein, said first and second insulators are integrally formed.

6. An oxygen sensor according to claim 1 further comprising:

an inside electrode disposed on an inner peripheral surface of said oxygen detecting element in such a manner that a gap of 0.1–0.3 mm is formed between said heating wire and said inside electrode.

\* \* \* \* \*